United States Patent [19]

Ueda et al.

[11] Patent Number: 5,229,290
[45] Date of Patent: Jul. 20, 1993

[54] REGENERATION METHOD OF INDIVIDUAL COCONUT PLANTLET

[75] Inventors: Shinta Ueda, Ichikai; Yukio Sugimura; Kazuya Otsuji, both of Utsunomiya; Wakayoshi Higashi, Wakayama; Kikuhiko Okamoto, Koshigaya, al of Japan

[73] Assignee: Kao Corporation, Tokyo, Japan

[21] Appl. No.: 869,832

[22] Filed: Apr. 16, 1992

Related U.S. Application Data

[63] Continuation of Ser. No. 574,528, Aug. 28, 1990, abandoned, which is a continuation of Ser. No. 247,600, Sep. 22, 1988, abandoned.

[30] Foreign Application Priority Data

Sep. 24, 1987 [JP] Japan ................................ 62-239347

[51] Int. Cl.$^5$ .............................................. A01H 4/00
[52] U.S. Cl. ........................ 435/240.51; 435/240.49; 435/240.54
[58] Field of Search ............ 800/DIG. 52; 435/240.4, 435/240.45, 240.46, 240.48, 240.49, 240.51, 240.54

[56] References Cited

PUBLICATIONS

Hu, et al. (1983) in Handbook of Plant Cell Culture, vol. 1 (Evans, et al. eds.) MacMillan Publishing Co., New York. pp. 206-208.
Branton, et al. (1983) New Scientist 98: pp. 554-557.
Gupta, et al. (1984) Plant Cell Reports 3: 222-225.
Colegrove (1983) Industrial and Engineering Chemistry Product Research and Development 22: pp. 456-460.
Physiol. Plant, vol. 36, pp. 23-28, 1976; C. J. Eeuwens.

*Primary Examiner*—Che S. Chereskin
*Attorney, Agent, or Firm*—Oblon, Spivak, McClelland, Maier & Neustadt

[57] ABSTRACT

A method is provided for the regeneration of an individual coconut plantlet. It comprises culturing a tissue explant of an undifferentiated male flower of a coconut tree in a culture medium, which contains 10-50 ppm of an auxin, 0.1-3% of a polysaccharide produced by a bacterium of Pseudomonas and 0.05-1% of activated carbon, in a dark place until a shoot-like structure appears; and then culturing under exposure to light of 3,000-20,000 luxes while repeating its subculture in a fresh culture medium.

2 Claims, No Drawings

REGENERATION METHOD OF INDIVIDUAL COCONUT PLANTLET

This application is a continuation of application Ser. No. 07/574,528 filed Aug. 28, 1990, now abandoned, which is a continuation of Ser. No. 07/247,600 filed Sep. 22, 1988, now abandoned.

BACKGROUND OF THE INVENTION

1) Field of the Invention

This invention relates to a method for regeneration of an individual coconut (*Cocos nucifera*) plantlet from cells of an undifferentiated male flower of a coconut tree.

2) Description of the Related Art

Coconut oil is an extremely important oil, which is useful as starting materials in various fields of the industry. Breeding of coconut has been attempted in recent years with a view toward increasing nut production. As a typical example of such breeding, hybridization between a dwarf variety and a tall variety is carried out in order to achieve heterosis. Hybrids resulted from such hybridization are reported to realize an increased yield of oil. Described specifically, breeding is effected (1) by mixed planting selected superior parent trees (mothers and fathers) in an isolated place and then allowing hybridization to occur under natural conditions so as to obtain a hybrid or (2) by artificially hybridizing between selected superior parent trees. However, the method (1) is accompanied by problems that an isolated wide field is essential and the resulting seeds may not exactly be the intended hybrid. The method (2) permits the provision of the intended hybrid without failure, but it is accompanied by a problem that a great deal of labor is required for hybridization and hybrid seeds cannot be obtained promptly in any large quantity.

Reflecting the recent advance in the technology of plant tissue culture, many attempts have been made on various species of plant so as to obtain clone plants having the genetically identical background to original plants. If this technique can be applied for the propagation of a coconut hybrid, many clone plantlets will be obtained promptly and easily from a single tree of elite hybrid having superior characters. This approach can hence be considered to be far superior to conventional propagation methods.

Eeuwens and Blake observed the development of various shoot-like structures upon culture of an undifferentiated male flower tissue of an unmatured inflorescence, and tried to regenerate individual plantlet from such shoot-like structures. They however failed to have the structures grow continuously into individual plantlets.

SUMMARY OF THE INVENTION

An object of this invention is to establish conditions for massive propagation of normal individual coconut plantlets, using an undifferentiated male flower tissue of a coconut tree, thereby providing a method for the regeneration of an individual coconut plantlet.

Under the circumstances as described above, the present inventors have carried out an extensive investigation with a view toward developing a method for the direct regeneration of an individual coconut plantlet from an undifferentiated male flower tissues of a coconut tree. As a result, it has been found that the above object can be attained by using a particular culture medium and choosing defined culturing conditions, leading to completion of this invention.

In one aspect of this invention, there is thus provided a method for the regeneration of an individual coconut plantlet, which comprises culturing a a tissue explant of an undifferentiated male flower of a coconut tree in a culture medium, which contains 10-50 ppm of an auxin, 0.1-3% of a polysaccharide produced by a bacterium of Pseudomonas and 0.05-1% of activated carbon, in a dark place until a shoot-like structure appears; and then culturing under exposure to light of 3,000-20,000 luxes while repeating its subculture in a fresh culture medium.

The present invention has made it possible to propagate a complete individual coconut plantlet from a piece of the tissue of an undifferentiated male flower of a coconut tree, whereby a method has been established for the massive production of a coconut hybrid.

The above and other objects, features and advantages of the present invention will become apparent from the following description and the appended claim.

DETAILED DESCRIPTION OF THE INVENTION AND PREFERRED EMBODIMENTS

As coconut trees useful in the practice of this invention, may be mentioned tall varieties, dwarf varieties, hybrids, etc. They are all usable suitably. The age of a coconut tree is optional. A coconut tree of a desired age, ranging from a coconut tree of such a young age as forming initial inflorescence to that having an age of several decades. As an inflorescence employed for obtaining an undifferentiated male flower tissue, that having a length of 10-150 mm is preferred.

An explant can be obtained in the following manner. An inflorescence of a matured coconut tree is taken out under aspic conditions. An undifferentiated male flower portion of the inflorescence is cut out with a thickness of 0.1-0.5 mm in Y-3 liquid culture medium of Eeuwens [Physiol. Plant., 36, 23 (1976)] or the like, so that an explant is provided. Needless to say, the culture medium employed here is not limited to the above-described Y-3 culture medium.

As a culture medium useful for the culture of the thus-obtained explant, a medium composed of inorganic compositions used in other established medium and a carbon source such as sugar added thereto may be provided as a basal medium, to which an auxin, a polysaccharide produced by a bacterium of Pseudomonas and activated carbon are added at final concentrations of 10-50 ppm, 0.1-3% and 0.05-1% respectively. In addition, vitamins, amino acids and other organic compositions may also be added as needed. As the basal medium, it is preferable to use Murashige-Skoog culture medium or Y-3 culture medium by way of example. It is also possible to use a culture medium obtained by improving the composition of such culture medium.

As auxins which may be added to the culture medium, may be mentioned 2,4-dichlorophenoxyacetic acid (2,4-D), naphthaleneacetic acid (NAA), indole butyric acid (IBA), etc. The auxin allows the undifferentiated male flower tissue to differentiate efficiently into true shootlet in the above concentration range. As another plant growth regulators, 6-benzyladenine (BA), isopentenyladenine (2-iP), kinetin, zeatin, gibberellin or the like may also be used suitably.

As exemplary polysaccharides produced by bacteria of Pseudomonas, the gums marketed in trade names such as "Gelrite gellan gum" (product of Merck & Co., Inc.) and "Gellan gum" (product of Merck & Co., Inc.) may be used preferably. Of these, heteropolysaccharides produced by *Pseudomonus eloda* are particularly preferred. Such polysaccharides may preferably be added at a concentration of 0.005-3%, notably, 0.1-0.4% to the medium.

The method of this invention is practised by culturing an explant of an undifferentiated male flower tissue of a coconut tree in a dark place until a shoot-like structure appears; and then culturing under exposure to light of 3,000-20,000 luxes. It is necessary to repeat subculture in a fresh culture medium during the culture period. Subculture may preferably be conducted at intervals of 0.5-1.5 months. The particularly preferable culture temperature may range from 25° C. to 30° C.

This invention will hereinafter be described in further detail by the following Example. It should however be borne in mind that the present invention is not necessarily limited to the following Example.

A coconut tree of an tall variety (about 30 years old) was cut down and inflorescences were cut out under sterile conditions. Their tissues were then sliced into pieces of 0.2 mm thick in liquid Y-3 basal medium so that explants were obtained. The explants were placed into a culture medium which have been supplemented by adding 2,4-D, BA, 2-iP, "Gellan gum" and activated carbon at concentrations of 20 ppm, 1 ppm, 1 ppm, 0.2% and 0.25% respectively to Y-3 basal medium. While repeating subculture onto a fresh culture medium, they were cultured at 28° C. for about 4 months in dark. In an initial stage of the culture, the explants expanded in size and 2-4 shoot-like structures were thereafter developed per an explant. Those structures grew a lot by transferring to the fresh culture medium. They were then cultured for about 6 months under exposure to light of 5,000 luxes for 16 hours a day while repeating subculture. Under the lighting conditions, the shoot-like structures changed from a white color to a greenish color and also changed into a true shootlet. At the same time, adventitious roots developed from the bottom portion of each shoot-like structure, so that from shoot-like structure a complete plantlet having both a shootlet and roots can be regenerated.

We claim:

1. A method for the regeneration of an individual coconut plantlet, which method comprises culturing a tissue explant of an undifferentiated male flower of a coconut tree in a culture medium, which medium contains 10-50 ppm of an auxin, 0.1-3% of gellan gum and 0.05-1% of activated carbon, in a dark place until a shoot-like structure appears; and then culturing the shoot-like structure under exposure to light of 3,000-20,000 lux such that a coconut plantlet is produced.

2. The method of claim 1, wherein the tissue explant is derived from an inflorescence of 10-150 mm in length.

* * * * *